United States Patent
Legrand

(10) Patent No.: US 7,226,486 B2
(45) Date of Patent: Jun. 5, 2007

(54) READY-TO-USE BLEACHING COMPOSITIONS, PREPARATION PROCESS AND BLEACHING PROCESS

(75) Inventor: Fréderic Legrand, Courbevoie (FR)

(73) Assignee: L'Oreal S.A, Paris (FR)

( * ) Notice: Subject to any disclaimer, the term of this patent is extended or adjusted under 35 U.S.C. 154(b) by 242 days.

(21) Appl. No.: 10/757,502

(22) Filed: Jan. 15, 2004

(65) Prior Publication Data

US 2004/0226110 A1    Nov. 18, 2004

Related U.S. Application Data

(60) Provisional application No. 60/441,322, filed on Jan. 22, 2003.

(30) Foreign Application Priority Data

Jan. 16, 2003  (FR) ................................. 03 00455

(51) Int. Cl.
D06L 3/02 (2006.01)

(52) U.S. Cl. .................. 8/101; 8/107; 8/109; 8/111; 8/552; 8/554; 8/561; 8/617; 132/202; 132/208; 424/62

(58) Field of Classification Search ............... 8/111, 8/431, 531, 552, 554, 561, 617, 101, 107, 8/109; 132/208, 202; 424/62
See application file for complete search history.

(56) References Cited

U.S. PATENT DOCUMENTS

| | | | |
|---|---|---|---|
| 2,261,002 A | 10/1941 | Ritter | 260/570 |
| 2,271,378 A | 1/1942 | Searle | 167/22 |
| 2,273,780 A | 2/1942 | Dittmar | 260/28 |
| 2,375,853 A | 5/1945 | Kirby et al. | 260/383 |
| 2,388,614 A | 11/1945 | Kirby et al. | 167/22 |
| 2,454,547 A | 11/1948 | Bock et al. | 255/587.6 |
| 2,961,347 A | 11/1960 | Floyd | 117/141 |
| 3,206,462 A | 9/1965 | McCarty | 260/256.4 |
| 3,227,615 A | 1/1966 | Korden | 167/87.1 |
| 3,472,840 A | 10/1969 | Stone et al. | 260/231 |
| 3,632,559 A | 1/1972 | Matter et al. | 260/78 |
| 3,836,537 A | 9/1974 | Boerwinkle et al. | 260/29.6 |
| 3,874,870 A | 4/1975 | Green et al. | 71/67 |
| 3,912,808 A | 10/1975 | Sokol | 424/71 |
| 3,915,921 A | 10/1975 | Schlatzer, Jr. | 260/17.4 |
| 3,917,817 A | 11/1975 | Vanlerberghe et al. | 424/70 |
| 3,929,990 A | 12/1975 | Green et al. | 424/78 |
| 3,966,904 A | 6/1976 | Green et al. | 424/78 |
| 3,986,825 A | 10/1976 | Sokol | 8/10.1 |
| 3,996,246 A | 12/1976 | Hoffmann et al. | 260/343.6 |
| 4,001,432 A | 1/1977 | Green et al. | 424/329 |
| 4,005,193 A | 1/1977 | Green et al. | 424/168 |
| 4,013,787 A | 3/1977 | Vanderbergue et al. | 424/70 |
| 4,025,617 A | 5/1977 | Green et al. | 424/78 |
| 4,025,627 A | 5/1977 | Green et al. | 424/298.4 |
| 4,025,653 A | 5/1977 | Green et al. | 424/325 |
| 4,026,945 A | 5/1977 | Green et al. | 260/567 |
| 4,027,008 A | 5/1977 | Sokol | 424/62 |
| 4,027,020 A | 5/1977 | Green et al. | 424/248.56 |
| 4,031,307 A | 6/1977 | DeMartino et al. | 536/114 |
| 4,131,576 A | 12/1978 | Iovine et al. | 260/17.4 |
| 4,157,388 A | 6/1979 | Christiansen | 424/70 |
| 4,172,887 A | 10/1979 | Vanlerberghe et al. | 424/70 |
| 4,189,468 A | 2/1980 | Vanlerberghe et al. | 424/70 |
| 4,197,865 A | 4/1980 | Jacquet et al. | 132/7 |
| 4,217,914 A | 8/1980 | Jacquet et al. | 132/7 |
| 4,240,450 A | 12/1980 | Grollier et al. | 132/7 |
| 4,277,581 A | 7/1981 | Vanlerberghe et al. | 525/420 |
| 4,349,532 A | 9/1982 | Vanlerberghe et al. | 424/47 |
| 4,381,919 A | 5/1983 | Jacquet et al. | 8/408 |
| 4,422,853 A | 12/1983 | Jacquet et al. | 8/406 |
| 4,445,521 A | 5/1984 | Grollier et al. | 132/7 |
| 4,509,949 A | 4/1985 | Huang et al. | 586/558 |
| 4,540,510 A | 9/1985 | Karl | 252/75.8 |
| 4,608,250 A | 8/1986 | Jacquet et al. | 424/71 |
| 4,702,906 A | 10/1987 | Jacquet et al. | 424/70 |
| 4,719,099 A | 1/1988 | Grollier et al. | 424/47 |
| 4,719,282 A | 1/1988 | Nadolsky et al. | 528/310 |
| 4,839,166 A | 6/1989 | Grollier et al. | 424/71 |
| 4,927,627 A | 5/1990 | Schrader et al. | 424/62 |

(Continued)

FOREIGN PATENT DOCUMENTS

EP    0 122 324 B2    2/1993

(Continued)

OTHER PUBLICATIONS

Fonnum, G., et al., "*Associative thickeners. Part I: Synthesis, rheology, and aggregation behavior,*" Colloid & Polymer Sci., 271:380-389 (1993).

(Continued)

*Primary Examiner*—Eisa Elhilo
(74) *Attorney, Agent, or Firm*—Finnegan, Henderson, Farabow, Garrett & Dunner

(57) ABSTRACT

Ready-to-use compositions for bleaching human keratin fibers, such as hair, comprising i) at least one anhydrous bleaching composition, in paste form, comprising at least one peroxygenated salt, at least one alkaline agent and from 1% to 35% by weight of at least one inert organic liquid, and ii) at least one oil-in-water emulsion comprising at least one first surfactant chosen from nonionic and anionic surfactants and at least one copolymer comprising (a) at least one unit derived from a salified or non-salified (meth)acrylic acid and (b) at least one unit derived from esters of (meth)acrylic acid and at least one first fatty alcohol chosen from saturated and unsaturated, linear and branched, ethoxylated $C_8$-$C_{30}$ fatty alcohols, wherein said ingredients (i) and (ii) are mixed before use; process for preparing the compositions; process for bleaching human keratin fibers using the compositions; and multicompartment devices comprising the compositions.

51 Claims, No Drawings

U.S. PATENT DOCUMENTS

| | | | |
|---|---|---|---|
| 4,948,579 A | 8/1990 | Jacquet et al. | 424/72 |
| 4,996,059 A | 2/1991 | Grollier et al. | 424/71 |
| 5,009,880 A | 4/1991 | Grollier et al. | 424/47 |
| 5,089,252 A | 2/1992 | Grollier et al. | 424/47 |
| 5,139,037 A | 8/1992 | Grollier et al. | 132/203 |
| 5,196,189 A | 3/1993 | Jacquet et al. | 424/72 |
| 5,888,484 A | 3/1999 | Schmitt et al. | 424/62 |
| 5,958,392 A | 9/1999 | Grollier et al. | 424/70.17 |
| 6,260,556 B1 | 7/2001 | Legrand et al. | 132/208 |
| 6,379,401 B1* | 4/2002 | Legrand et al. | 8/431 |
| 6,540,791 B1* | 4/2003 | Dias | 8/111 |
| 2002/0152556 A1* | 10/2002 | Ascione et al. | 8/405 |
| 2002/0157191 A1 | 10/2002 | Casperson et al. | 8/405 |
| 2004/0074015 A1 | 4/2004 | Kravtchenko et al. | 8/406 |

FOREIGN PATENT DOCUMENTS

| | | |
|---|---|---|
| EP | 0 337 354 B1 | 2/1994 |
| EP | 0 216 479 B2 | 8/1994 |
| EP | 0 882 444 A | 12/1998 |
| EP | 1 036 558 B1 | 9/2000 |
| FR | 1 492 597 | 8/1967 |
| FR | 1 583 363 | 10/1969 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 413 907 | 8/1979 |
| FR | 2 470 596 | 6/1981 |
| FR | 2 519 863 | 7/1983 |
| FR | 2 598 611 | 11/1987 |
| FR | 2 633 940 | 1/1990 |
| FR | 2 788 974 | 8/2000 |
| FR | 2 788 976 | 8/2000 |
| FR | 2 818 540 | 12/2000 |
| GB | 1347051 | 2/1974 |
| GB | 1479786 | 7/1977 |
| GB | 1546809 | 5/1979 |
| JP | A H1-106813 | 4/1989 |
| JP | A H9-157142 | 6/1997 |
| JP | A H11-12140 | 1/1999 |
| JP | A 2000-309518 | 11/2000 |
| JP | A 2001-2474437 | 9/2001 |
| JP | A 2002-29946 | 1/2002 |
| WO | WO 03/000212 A2 | 1/2003 |

OTHER PUBLICATIONS

English language Derwent Abstract of EP 0 882 444, dated Dec. 9, 1998.

English language Derwent Abstract of FR 2 633 940.

French Search Report, dated Oct. 9, 2003.

Pepe, R.C.; Wenninger, J. A.; and McEwen, G. N., "International Cosmetic Ingredient Dictionary and Handbook," *The Cosmetic, Toiletry and Fragrance Association,* 1:28-32 (2002).

English language Derwent Abstract of JP-A 2002-29946, Jan. 29, 2002.

* cited by examiner

READY-TO-USE BLEACHING COMPOSITIONS, PREPARATION PROCESS AND BLEACHING PROCESS

This application claims benefit of U.S. Provisional Application No. 60/441,322, filed Jan. 22, 2003.

Disclosed herein is a composition for bleaching keratin fibers, a process for bleaching keratin fibers using the composition and a multi-compartment device comprising the composition.

It is known practice to bleach human keratin fibers, such as hair, using bleaching compositions comprising at least one oxidizing agent. Examples of oxidizing agents conventionally used include hydrogen peroxide or compounds capable of producing hydrogen peroxide by hydrolysis, such as urea or persalts such as perborates, persulphates and percarbonates.

Originally, bleaching compositions were in powder form, i.e., pulverulent compositions. However, they had the drawback of producing dust during their handling, transportation and storage. Furthermore, this phenomenon could be aggravated by the fact that the products of which these powders were composed could be corrosive and irritant to the eyes, the respiratory pathways and mucous membranes. Accordingly, in order to solve at least some of these problems encountered during the use of pulverulent compositions, bleaching compositions in paste form have recently been developed. Thus, the pulverulent compounds are dispersed in a thickened organic inert liquid support.

Although this presentation form can provide a solution to at least some of the volatility problems mentioned above, the use of compositions in paste form may result in new difficulties.

Thus, the bleaching compositions, whether in powder or paste form, usually need to be mixed before use with an oxidizing agent, such as aqueous hydrogen peroxide compositions, in order to obtain a ready-to-use bleaching composition.

These aqueous hydrogen peroxide compositions may be in the form of aqueous solutions or oil-in-water emulsions and may be more or less liquid or fluid.

This presentation form may favor mixtures with bleaching compositions in powder form, because the more liquid or fluid the aqueous hydrogen peroxide composition, the more quickly and easily the bleaching powder may dissolve.

On the other hand, bleaching compositions in paste form lack water and their texture may be compact and hard. Furthermore, these bleaching pastes are of hydrophobic nature given the presence of a high content of inert organic liquid. Consequently, the mixing of the bleaching composition and of the hydrogen peroxide composition may not be easy. This may be reflected not only by a longer mixing time but also by a complication of the operations to obtain a uniform mixture.

One of the solutions envisaged in the art was to enrich the hydrogen peroxide oil-in-water emulsions with fatty substances such as fatty alcohols, in order to obtain more compact cream textures. However, there is a great difference in texture between these compositions and the known anhydrous bleaching pastes, and the mixtures may take a relatively long time to prepare.

It would thus be beneficial to find oxidizing aqueous compositions which mix with bleaching pastes more quickly and more easily.

The aim of the present inventors is to solve at least one of the problems mentioned above.

Thus, disclosed herein is a ready-to-use composition for bleaching human keratin fibers, such as hair, comprising:

i) at least one anhydrous bleaching composition, in paste form, comprising:
  at least one peroxygenated salt;
  at least one alkaline agent; and
  from 15% to 35% by weight of at least one inert organic liquid; and
ii) at least one hydrogen peroxide oil-in-water emulsion comprising:
  at least one first surfactant chosen from nonionic and anionic surfactants and
  at least one copolymer comprising (a) at least one unit derived from a salified or non-salified (meth)acrylic acid and (b) at least one unit derived from esters of (meth)acrylic acid and at least one first fatty alcohol chosen from saturated and unsaturated, linear and branched, ethoxylated $C_8$-$C_{30}$ fatty alcohols, wherein the at least one anhydrous bleaching composition and the at least one hydrogen peroxide oil-in-water emulsion are mixed before use.

Further disclosed herein is a process for preparing the composition, comprising mixing before use the at least one anhydrous bleaching composition, in paste form, and the at least one hydrogen peroxide oil-in-water emulsion.

Even further disclosed herein is a process for bleaching human keratin fibers, such as hair, comprising applying at least one ready-to-use bleaching composition as disclosed herein to the area of wet or dry human keratin fibers to be bleached; leaving the at least one ready-to-use composition to act for a leave-in time that is sufficient to obtain the desired bleaching; removing the at least one ready-to-use composition from the human keratin fibers by rinsing with water, washing the human keratin fibers with shampoo, and optionally drying the human keratin fibers.

Also disclosed herein is a multi-compartment device, or "kit", for performing the abovementioned bleaching process, comprising at least two compartments, wherein at least one compartment comprises at least one anhydrous bleaching composition, in paste form, comprising:
  at least one peroxygenated salt,
  at least one alkaline agent, and
  from 15% to 35% by weight of at least one inert organic liquid; and
at least one other compartment comprises at least one hydrogen peroxide oil-in-water emulsion comprising:
  at least one first surfactant chosen from nonionic and anionic surfactants and
  at least one copolymer comprising (a) at least one unit derived from a salified or non-salified (meth)acrylic acid and (b) at least one unit derived from esters of (meth)acrylic acid and at least one first fatty alcohol chosen from saturated and unsaturated, linear and branched, ethoxylated $C_8$-$C_{30}$ fatty alcohols.

It has been found that mixtures of at least one anhydrous bleaching composition, in paste form, and at least one hydrogen peroxide ON emulsion comprising at least one first surfactant chosen from nonionic and anionic surfactants and at least one copolymer as described above, may be prepared significantly more quickly and more easily than previously known mixtures.

Furthermore, the ready-to-use bleaching compositions disclosed herein may be easy and quick to apply. These compositions may show very good adhesion and may not run outside the areas that it is desired to bleach.

The disclosed ready-to-use bleaching compositions may also allow strong, uniform bleaching results, while at the same time providing at least one very good cosmetic property.

Other characteristics and advantages of the various embodiments disclosed herein will emerge more clearly on reading the description and the examples that follow.

The at least one anhydrous bleaching composition will first be described.

Anhydrous Bleaching Composition

As indicated previously, the at least one anhydrous composition is in paste form. For example, the at least one anhydrous composition may comprise less than 1% by weight of water and, further, for example, less than 0.5% by weight of water, relative to the total weight of the at least one anhydrous bleaching composition.

Peroxygenated Salt

The at least one anhydrous bleaching composition comprises at least one peroxygenated salt, which may be chosen, for example, from persulfates, perborates, percarbonates and peroxides of alkali metals and alkaline-earth metals, such as sodium, potassium and magnesium.

In one embodiment, the at least one anyhydrous bleaching composition may comprise, as the at least one peroxygenated salt, at least one alkali metal persulphate chosen from sodium persulphate and potassium persulphate.

For example, the at least one peroxygenated salt may be present in the at least one anhydrous bleaching composition in an amount ranging from 10% to 70% by weight, and further, for example, from 20% to 60% by weight, relative to the total weight of the at least one anhydrous bleaching composition.

It should be noted that, for example, the at least one peroxygenated salt in the ready-to-use composition may be present in an amount ranging from 5% to 35% by weight, relative to the total weight of the ready-to-use composition (i.e. comprising the mixture of the at least one anhydrous bleaching composition and the at least one hydrogen peroxide oil-in-water emulsion) and further, for example, ranging from 10% to 30% by weight, relative to the total weight of the ready-to-use composition.

Alkaline Agents

The at least one anhydrous bleaching composition also comprises at least one alkaline agent, which may, for example, be chosen from urea; ammonium salts, such as chlorides, sulphates, phosphates and nitrates; and alkali metal, such as sodium and potassium, and alkaline-earth metal, such as magnesium, silicates, phosphates and carbonates.

For example, the at least one alkaline agent in the at least one anhydrous bleaching composition may be present in an amount ranging from 0.01% to 40% by weight and further, for example, from 0.1% to 30% by weight, relative to the total weight of the at least one anhydrous bleaching composition. In one embodiment, the at least one alkaline agent in the ready-to-use composition is present in an amount ranging, for example, from 0.005% to 20% by weight and, further, for example, from 0.05% to 15% by weight, relative to the total weight of the ready-to-use composition.

Inert Liquid

The at least one anhydrous bleaching composition further comprises from 15% to 35% by weight of at least one inert organic liquid.

The term "liquid" means a compound or a mixture of compounds that is liquid at 25° C. and at atmospheric pressure.

For example, the at least one inert organic liquid may be chosen from polydecenes; carboxylic acid monoesters and polyesters; sugar monoesters and polyesters of $C_8$-$C_{30}$ acids; cyclic ethers; cyclic esters; silicone oils; mineral oils; and plant oils.

For example, the polydecenes may be chosen from compounds of formula $C_{10n}H_{[(20n)+2]}$ wherein n is a number ranging, for example, from 3 to 9 and, further, for example, from 3 to 7. These compounds correspond to the name "polydecene" in the CTFA Dictionary 7th edition 1997, of the Cosmetics, Toiletry and Fragrance Association, USA, and also to the same INCI name in the USA and in Europe. They are poly-1-decene hydrogenation products.

Examples of polydecenes include the product sold under the name SILKFLO 366 NF Polydecene by the company Amoco Chemical and the products sold under the name NEXBASE 2002 FG, 2004 FG, 2006 FG and 2008 FG by the company Fortum.

As for the carboxylic acid monoesters and polyesters which may, for example, be chosen from linear and branched, and saturated and unsaturated carboxylic acid monoesters and polyesters, they may, for example, comprise at least one hydrocarbon-based chain comprising from $C_8$-$C_{30}$ carbons, further, for example, from $C_8$-$C_{24}$ carbons and, even further, for example, from $C_{12}$-$C_{24}$ carbons, derived from the acid or alcohol portion. The carboxylic acid monoesters and polyesters may also comprise, for example, at least one other hydrocarbon-based chain comprising, for example, from $C_1$-$C_8$ carbons, and further, for example, from $C_1$-$C_6$ carbons. Furthermore, if the carboxylic acid comprises several carboxylic functional groups, these functional groups may, for example, all be esterified. It should be noted that the alcohols may, for example, be monofunctional alcohols.

Examples that may be mentioned include esters of oleic acid, lauric acid, palmitic acid, myristic acid, behenic acid, stearic acid, linoleic acid, linolenic acid, capric acid, arachidonic acid, and mixtures thereof, such as, oleo-palmitic, oleo-stearic, palmito-stearic, etc. mixtures.

Further examples include isopropyl diester of sebacic acid (diisopropyl sebacate), dioctyl adipate and dicaprylyl maleate.

Furthermore, it may also be possible to use a polyester of (a) a polycarboxylic acid comprising at least one radical chosen from saturated and unsaturated, linear and branched radicals comprising less than 6 carbon atoms, and of (b) an alcohol comprising at least one radical chosen from saturated and unsaturated, linear and branched radicals comprising less than 6 carbon atoms. An example of the polyester of a polycarboxylic acid is triethyl citrate.

For example, the esters may be chosen, from esters obtained from $C_{12}$-$C_{24}$ fatty acids, for example, comprising at least one carboxylic group, and from saturated, linear and branched $C_3$-$C_6$ monoalcohols.

For example, the at least one anhydrous bleaching composition may comprise, as the at least one inert liquid, isopropyl palmitate and, further, for example, isopropyl myristate, alone or as mixtures.

With regard to the sugar monoesters and polyesters of $C_8$-$C_{30}$, for example, $C_{12}$-$C_{24}$, acids, it is pointed out that the term "sugar" means compounds comprising several hydroxyl functional groups, with or without an aldehyde or ketone functional group, and which comprise at least 4 carbon atoms. These sugars may be chosen from monosaccharides, oligosaccharides and polysaccharides. Examples of suitable sugars include sucrose (or saccharose), glucose, galactose, ribose, fucose, maltose, fructose, mannose, arabinose, xylose and lactose, and derivatives thereof, for example, alkyl derivatives, such as methyl derivatives, for example, methylglucose.

With regard to the saturated and unsaturated, linear and branched $C_8$-$C_{30}$ acids, comprising one or two carboxylic functional groups, reference may be made to the lists given previously.

The esters may, for example, be chosen from at least one of monoesters, diesters, triesters, tetraesters and polyesters.

For example, the esters may be chosen from monoesters and diesters, such as saccharose, glucose and methylglucose monooleates, monostearates, monobehenates, monooleopalmitates, monolinoleates, monolinolenates, monooleostearates dioleates, distearates, dibehenates, dioleopalmitates, dilinoleates, dilinolenates and dioleostearates.

Examples of the monoesters and diesters include the product sold under the name GLUCATE DO by the company Amerchol, which is a methylglucose dioleate, the products sold under the names F160, F140, F110, F90, F70 and SL40 by the company Crodesta, respectively denoting sucrose palmitostearates formed of 73% monoester and 27% diester and triester; 61% monoester and 39% diester, triester and tetraester; 52% monoester and 48% diester, triester and tetraester; 45% monoester and 55% diester, triester and tetraester; 39% monoester and 61% diester, triester and tetraester; and sucrose monolaurate; the products sold under the name RYOTO Sugar Esters, for example referenced B370 and corresponding to sucrose behenate formed of 20% monoester and 80% di-triester-polyester; sucrose mono-di-palmitostearate sold by the company Goldschmidt under the name TEGOSOFT PSE.

With regard to the cyclic esters and ethers, examples include γ-butyrolactone, dimethyl isosorbide (CTFA name), and diisopropyl isosorbide (CTFA name).

With regard to the silicone oils, compounds that are, for example, liquid and non-volatile may be used as the at least one inert liquid, for example, with a viscosity of less than or equal to 10 000 mPa.s at 25° C., the viscosity of the silicones being measured according to ASTM standard 445 Appendix C.

Silicone oils are defined in greater detail in Walter Noll's "Chemistry and Technology of Silicones" (1968)—Academic Press.

Examples of suitable silicone oils, include the silicone oils sold under the names DC-200 Fluid-5 mPa.s, DC-200 Fluid-20 mPa.s, DC-200 Fluid-350 mPa.s, DC-200 Fluid-1 000 mPa.s and DC-200 Fluid-10 000 mPa.s by the company Dow Corning.

Liquid paraffin is an example of a mineral oil that may be used as the at least one inert liquid in the at least one anhydrous bleaching composition.

With regard to the plant oils, examples include avocado oil, olive oil and liquid jojoba wax.

Additives

Amphiphilic Polymers:

The at least one anhydrous bleaching composition may further comprise at least one common additive such as at least one amphiphilic polymer comprising at least one hydrophobic chain. For example, when the at least one amphiphilic polymer is present, it may be chosen from nonionic, anionic, cationic and amphoteric amphiphilic polymers. The at least one amphiphilic polymer may, for example, be of nonionic, anionic or cationic nature.

It should be noted that the at least one amphiphilic polymer present in the at least one anhydrous bleaching composition and the at least one copolymer present in the at least one hydrogen peroxide oil-in-water emulsion, which will be described in detail later, may, for example, be different.

For example, the at least one amphiphilic polymer may comprise, as the at least one hydrophobic chain, a chain chosen from saturated and unsaturated, aromatic and non-aromatic, linear and branched $C_8$-$C_{30}$ hydrocarbon-based chains, optionally comprising at least one oxyalkylene (oxyethylene and/or oxypropylene) unit.

The cationic amphiphilic polymers comprising at least one hydrophobic chain may, for example, be chosen from cationic polyurethanes and cationic copolymers comprising at least one vinyllactam unit, such as a vinylpyrrolidone unit.

Even further, for example, the at least one amphiphilic polymer comprising at least one hydrophobic chain may be chosen from nonionic amphiphilic polymers comprising at least one hydrophobic chain and anionic amphiphilic polymers comprising at least one hydrophobic chain.

For example, the non-ionic amphiphilic polymers comprising at least one hydrophobic chain may be chosen from:
(1) celluloses modified with groups comprising at least one hydrocarbon-based chain chosen from saturated and unsaturated, linear and branched $C_6$-$C_{30}$ hydrocarbon-based chains, for example, hydroxyethylcelluloses modified with groups comprising at least one hydrophobic chain as defined previously, for example, NATROSOL Plus Grade 330 CS ($C_{16}$ alkyl—sold by the company Aqualon); BERMOCOLL EHM 100 (sold by the company Berol Nobel), AMERCELL Polymer HM-1500 (hydroxyethylcellulose modified with a polyethylene glycol (15) nonylphenyl ether group—sold by the company Amerchol);
(2) hydroxypropylguars modified with groups comprising at least one hydrophobic chain as defined above, for example JAGUAR XC-95/3 ($C_{14}$ alkyl chain—sold by the company Rhodia Chimie); ESAFLOR HM 22 ($C_{22}$ alkyl chain—sold by the company Lamberti); RE210-18 ($C_{14}$ alkyl chain) and RE205-1 ($C_{20}$ alkyl chain) sold by the company Rhodia Chimie;
(3) copolymers of vinylpyrrolidone and of hydrophobic monomers comprising at least one hydrophobic chain as defined above, for example, ANTARON and GANEX V216 (vinylpyrrolidone/hexadecene copolymers); ANTARON and GANEX V220 (vinylpyrrolidone/eicosene copolymers), sold by the company I.S.P;
(4) copolymers of $C_1$-$C_6$ alkyl (meth)acrylates and of amphiphilic monomers comprising at least one hydrophobic chain;
(5) copolymers of hydrophilic (meth)acrylates and of hydrophobic monomers comprising at least one hydrophobic chain, for example, a polyethylene glycol methacrylate/lauryl methacrylate copolymer;
(6) polymers with an aminoplast ether skeleton comprising at least one fatty chain, such as the PURE THIX compounds sold by the company Süd-Chemie; and
(7) linear (block structure), grafted and starburst polyurethanepolyethers comprising, in their chain, at least one hydrophilic block, which is generally a polyoxyethylene block which may comprise from 50 to 1 000 oxyethylene units, and at least one hydrophobic block, which may comprise aliphatic groups alone, optionally combined with cycloaliphatic and/or aromatic sequences. For example, the polyurethanepolyethers may comprise at least two $C_6$-$C_{30}$ hydrocarbon-based hydrophobic chains, separated by the at least one hydrophilic block; the hydrophobic chains may be pendent chains or chains with at least one of the end groups of the at least one hydrophilic block;

The polyurethanepolyethers may comprise a urethane bond between the hydrophilic blocks, hence the name. By extension, polyurethanepolyethers wherein the at least one hydrophilic block is linked to lipophilic blocks via other chemical bonds may also be included.

The polyurethanepolyethers that may be used in the compositions disclosed herein include those described in the article by G. Formum, J. Bakke and Fk. Hansen—Colloid Polym. Sci. 271, 380.389 (1993). Further examples of polyurethanepolyethers include NUVIS FX 1100 (European and US INCI name "Steareth-100/PEG-136/HMDI Copolymer" sold by the company Servo Delden); RHÉOLATE 205, 208, 204 or 212 (sold by the company Rheox); ELFACOS T210 ($C_{12}$-$C_{14}$ alkyl chain) and ELFACOS T212 ($C_{18}$ alkyl chain) sold by the company Akzo.

The anionic amphiphilic polymers comprising at least one hydrophobic chain that may be used herein may comprise, as the at least one hydrophobic chain, at least one hydrocarbon-based chain chosen from saturated and unsaturated, aromatic and non-aromatic, linear and branched $C_8$-$C_{30}$ hydrocarbon-based chains.

For example, the anionic amphiphilic polymers comprising at least one hydrophobic chain that may be used in the compositions disclosed herein, which may be crosslinked or non-crosslinked, comprise at least one hydrophilic unit derived from at least one ethylenically unsaturated monomer bearing a free carboxylic acid functional group, or a sulphonic functional group which is free or partially or totally neutralized, and at least one hydrophobic unit derived from at least one ethylenically unsaturated monomer bearing at least one hydrophobic side chain, and optionally at least one crosslinking unit derived from at least one polyunsaturated monomer.

The at least one ethylenically unsaturated monomer bearing a carboxylic acid functional group may be chosen, for example, from ethacrylic acid, methacrylic acid and acrylic acid; the last two monomers may, for example, be used.

The at least one ethylenically unsaturated monomer bearing at least one hydrophobic side chain may, for example, be chosen from esters of unsaturated carboxylic acids such as ethacrylic acid, methacrylic acid and acrylic acid, and of alcohols chosen from saturated, linear and branched, $C_{10}$-$C_{30}$, for example, $C_{12}$-$C_{22}$, alcohols. The at least one ethylenically unsaturated monomer bearing at least one hydrophobic side chain may also, for example, be chosen from allylic ethers of alcohols chosen from saturated and unsaturated, aromatic and non-aromatic, branched and unbranched $C_6$-$C_{30}$ alcohols, which are optionally oxyalkylenated, for example, oxyethylenated. The allylic ethers may, for example, be of formula $CH_2=CR'CH_2OB_nR$ wherein R' is chosen from H and $CH_3$, B is an ethylenoxy radical, n is an integer ranging from 0 to 100, R is a hydrocarbon-based radical chosen from alkyl, arylalkyl, aryl, alkylaryl and cycloalkyl radicals comprising from 8 to 30 carbon atoms. For example, the unit may be such that R' is hydrogen, n is equal to 10 and R is a stearyl ($C_{18}$) radical.

With regard to the at least one crosslinking monomer, this monomer may comprise at least two polymerizable double bonds that are not conjugated with each other. For example, the at least one crosslinking monomer may be chosen from diallylphthalate, allyl (meth)acrylate, divinylbenzene, (poly) ethylene glycol dimethacrylate, methylenebisacrylamide, polyallylsucrose and polyallylpentaerythritol.

Anionic amphiphilic polymers of the type described above are described and prepared, for example, in U.S. Pat. Nos. 3,915,921 and 4,509,949 (copolymers of (meth)acrylic acid and of $C_{10}$-$C_{30}$ alkyl (meth)acrylates) or in EP Patent No. 216 479 (copolymers of (meth)acrylic acid and of fatty alkyl allyl ethers).

Examples of the anionic amphiphilic polymers of the type described above include CARBOPOL ETD 2020 (acrylic acid/$C_{10}$-$C_{30}$ alkyl methacrylate crosslinked copolymer—sold by the company Goodrich); CARBOPOL 1382, PEMULEN TR1 and PEMULEN TR2 (acrylic acid/$C_{10}$-$C_{30}$ alkyl acrylate crosslinked copolymers—sold by the company Goodrich).

The amphiphilic polymers comprising, as the at least one hydrophilic unit, at least one ethylenically unsaturated monomer comprising a sulphonic group, in free or partially or totally neutralized form and at least one hydrophobic portion are described, for example, in FR 00/16954 and FR 01/00328, the disclosures of which relating to such amphiphilic polymers form an integral part of the present disclosure.

Examples of such amphiphilic polymers include acrylamido-2-methyl-2-propanesulphonic (AMPS) acid/n-dodecylacrylamide copolymer neutralized with sodium hydroxide, the copolymer crosslinked with methylenebisacrylamide consisting of 75% by weight of AMPS units neutralized by $NH_3$ and 25% by weight of Genapol T-250 acrylate units, the copolymer crosslinked with allyl methacrylate consisting of 90% by weight of AMPS units neutralized with $NH_3$ and 10% by weight of Genapol T-250 methacrylate units, or the copolymer crosslinked with allyl methacrylate consisting of 80% by weight of AMPS units neutralized with $NH_3$ and 20% by weight of Genapol T-250 methacrylate units.

When the at least one amphiphilic polymer comprising at least one hydrophobic chain is present, its content ranges from 0.01% to 30% by weight, relative to the total weight of the ready-to-use bleaching composition.

Water-soluble thickening polymers not comprising a hydrophobic chain:

The at least one anhydrous bleaching composition may further comprise at least one water-soluble thickening polymer not comprising a hydrophobic chain.

The at least one water-soluble thickening polymer may, for example, be chosen from polymers of natural origin and synthetic polymers, and, further, for example, may be chosen from those conventionally used in cosmetics. In addition, the at least one water-soluble thickening polymer does not contain a hydrophobic chain, i.e., a saturated or unsaturated, aromatic or non-aromatic, linear or branched $C_8$-$C_{30}$ hydrocarbon-based chain, optionally comprising at least one oxyalkylene (oxyethylene and/or oxypropylene) unit. The at least one water-soluble thickening polymer is thus different from the at least one amphiphilic polymer that has just been described.

The synthetic polymers may, for example, be chosen from polyvinylpyrrolidone, polyacrylic acid, polyacrylamide, non-crosslinked poly(2-acrylamidopropanesulphonic acid) (SIMUGEL EG from the company SEPPIC), crosslinked poly(2-acrylamido-2-methylpropanesulphonic acid), free and partially neutralized with ammonia (HOSTACERIN AMPS from Clariant), mixtures of non-crosslinked poly(2-acrylamido-2-methylpropanesulphonic acid) with hydroxyalkylcellulose ethers and with poly(ethylene oxides), as described in U.S. Pat. No. 4,540,510; mixtures of poly ((meth)acrylamido($C_1$-$C_4$)alkylsulphonic acid), which may, for example, be crosslinked with a crosslinked copolymer of maleic anhydride and a ($C_1$-$C_5$)alkyl vinyl ether (HOSTACERIN AMPS/STABILEZE QM from the company ISF).

The thickening polymers of natural origin may, for example, be chosen from polymers comprising at least one sugar unit, for example, nonionic guar gums, optionally modified with at least one $C_1$-$C_6$ hydroxyalkyl group; biopolysaccharide gums of microbial origin, such as scleroglucan gum and xanthan gum; gums derived from plant exudates, such as gum arabic, ghatti gum, karaya gum, gum tragacanth, carrageenan gum, agar gum and carob gum; pectins; alginates; starches; hydroxy($C_1$-$C_6$)alkylcelluloses and carboxy($C_1$-$C_6$)alkylcelluloses.

As used herein, the term "sugar unit" means a monosaccharide (i.e., monosaccharide or oside or simple sugar) portion, an oligosaccharide portion (short chains formed from a sequence of monosaccharide units, which may be different) or a polysaccharide portion [long chains consisting of monosaccharide units, which may be different, i.e. polyholosides or polyosides]. The saccharide units may also be substituted with at least one substituent chosen from alkyl, hydroxyalkyl, alkoxy, acyloxy and carboxyl substituents, the alkyl radicals comprising from 1 to 4 carbon atoms.

Examples of nonionic, unmodified guar gums include GUARGEL D/15 (Goodrich); VIDOGUM GH 175 (Unipectine), MAYPRO-GUAR 50 and JAGUAR C (Meyhall/Rhodia Chimie); and examples of the modified nonionic guar gums include JAGUAR HP8, HP60, HP120, DC 293 and HP 105 (Meyhall/Rhodia Chimie); GALACTASOL $4H_4FD2$ (Aqualon).

The biopolysaccharide gums of microbial or plant origin are well known to those skilled in the art and are described, for example, in the book by Robert L. Davidson entitled "Handbook of Water Soluble Gums and Resins" published by McGraw Hill Book Company (1980).

Examples of these gums include scleroglucans such as, ACTIGUM CS from Sanofi Bio Industries; AMIGEL from Alban Muller International, and also the glyoxal-treated scleroglucans described in French Patent No. 2 633 940; xanthan gums, for example, KELTROL, KELTROL T, KELTROL Tf, KELTROL Bt, KELTROL Rd, KELTROL Cg (Nutrasweet Kelco), RHODICARE S and RHODICARE H (Rhodia Chimie); starch derivatives, for example, PRIMOGEL (Avebe); hydroxyethylcelluloses such as CELLOSIZE QP3L, QP4400H, QP30000H, HEC30000A and Polymer PCG10 (Amerchol), NATROSOL 250HHR, 250MR, 250M, 250HHXR, 250HHX, 250HR, HX (Hercules) and TYLOSE H1000 (Hoechst); hydroxypropylcelluloses, for example, KLUCEL EF, H, LHF, MF and G (Aqualon); carboxymethylcelluloses, for example, BLANOSE 7M8/SF, refined 7M, 7LF, 7MF, 9M31F, 12M31XP, 12M31P, 9M31XF, 7H, 7M31, 7H3SXF (Aqualon), AQUASORB A500 (Hercules), AMBERGUM 1221 (Hercules), CELLOGEN HP810A, HP6HS9 (Montello) and PRIMELLOSE (Avebe).

When the at least one water-soluble thickening polymer not containing a hydrophobic chain is present, its content ranges from 0.01% to 30% by weight, relative to the total weight of the at least one anhydrous bleaching composition.

Surfactants:

The at least one anhydrous bleaching composition may also comprise at least one second surfactant chosen from anionic, nonionic, cationic and amphoteric surfactants.

For example, the anionic surfactants that can be used in the compositions disclosed herein may chosen from at least one salt, for example, alkali metal salts such as sodium salts, ammonium salts, amine salts, amino alcohol salts and magnesium salts, of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; ($C_6$-$C_{24}$)alkyl sulphosuccinates, ($C_6$-$C_{24}$)alkyl ether sulphosuccinates, ($C_6$-$C_{24}$)alkylamide sulphosuccinates; ($C_6$-$C_{24}$)alkyl sulphoacetates; ($C_6$-$C_{24}$)acyl sarcosinates and ($C_6$-$C_{24}$)acyl glutamates. It is also possible to use ($C_6$-$C_{24}$) alkylpolyglycoside carboxylic esters such as alkylglycoside citrates, alkylglycoside tartrates and alkylglycoside sulphosuccinates, alkylsulphosuccinamates; acyl isethionates and N-acyl taurates, wherein the alkyl or acyl radical of all of these different compounds, for example, comprises from 12 to 20 carbon atoms and the aryl radical may, for example, be chosen from a phenyl and a benzyl group.

The anionic surfactants may also, for example, be chosen from fatty acid salts such as oleic, ricinoleic and palmitic acid salts, coconut oil acid and hydrogenated coconut oil acid, and, for example, sodium, calcium and magnesium salts of stearic acid; acyl lactylates wherein the acyl radical comprises from 8 to 20 carbon atoms. It is also possible to use alkyl D-galactoside uronic acids and the salts thereof, polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$)alkylamido ether carboxylic acids and the salts thereof, for example, those comprising from 2 to 50 alkylene oxide groups, for example, ethylene oxide groups, and mixtures thereof.

Without wishing to be limited thereto, the nonionic surfactants may also be chosen, for example, from at least one of polyethoxylated and polypropoxylated, alkylphenols, alpha-diols and alcohols, comprising at least one chain comprising, for example, from 8 to 22 carbon atoms, it being possible for the number of ethylene oxide and/or propylene oxide groups to range, for example, from 1 to 50. Further examples also include copolymers of ethylene oxide and of propylene oxide, condensates of ethylene oxide and of propylene oxide with fatty alcohols (comprising, for example, from 8 to 22 carbon atoms); polyethoxylated fatty amides (for example $C_8$-$C_{22}$) for example, comprising from 2 to 30 mol of ethylene oxide, monoglycerolated and polyglycerolated fatty alcohols (for example $C_8$-$C_{22}$) comprising on average from 1 to 30 glycerol groups and polyglycerolated fatty amides comprising on average from 1 to 5, and, for example, from 1.5 to 4 glycerol groups; oxyethylenated fatty acid esters (for example $C_8$-$C_{22}$) of sorbitan, for example, comprising from 2 to 30 mol of ethylene oxide; fatty acid esters (for example $C_8$-$C_{22}$) of sucrose, fatty acid esters (for example $C_8$-$C_{22}$) of polyethylene glycol, alkylpolyglycosides, N-alkylglucamine derivatives, and amine oxides such as ($C_{10}$-$C_{14}$)alkylamine oxides and N-acylaminopropyl-morpholine oxides.

For example, the amphoteric or zwitterionic surfactants may further be chosen from aliphatic secondary and tertiary amine derivatives wherein the aliphatic radical is chosen from linear and branched $C_8$-$C_{18}$ chains comprising at least one anionic group chosen from carboxylate, sulphonate, sulphate, phosphate and phosphonate groups; ($C_8$-$C_{20}$)alkylbetaines, ($C_8$-$C_{20}$)alkylsulphobetaines, ($C_8$-$C_{20}$)alkylamido($C_1$-$C_6$)alkylbetaines and ($C_8$-$C_{20}$)alkylamido($C_1$-$C_6$)alkylsulphobetaines. Further examples include ampho-carboxyglycinates and ampho-carboxypropionates, classified in the CTFA dictionary, 5th edition, 1993, under the names Disodium Cocoamphodiacetate, Disodium Lauroamphodiacetate, Disodium Caprylamphodiacetate, Disodium Caproamphodiacetate, Disodium Cocoamphodipropionate, Disodium Lauroamphodipropionate, Disodium Caprylamphodipropionate, Disodium Caprylloamphodipropionate, Lauroamphodipropionic acid and Cocoamphodipropionic acid. For example, mention may be made of Cocoamphodiacetate (Miranol® C2M Concentrate from Rhodia Chimie).

The cationic surfactants may be chosen from: salts of optionally polyoxyalkylenated primary, secondary and tertiary fatty amines; quaternary ammonium salts such as tetraalkylammonium, alkylamidoalkyltrialkylammonium, trialkylbenzylammonium, trialkylhydroxyalkylammonium and alkylpyridinium chlorides and bromides; imidazoline derivatives; and amine oxides of cationic nature.

For example, when the at least one second surfactant is present, it may be chosen from anionic and nonionic compounds.

When at least one second surfactant is present in the at least one anhydrous bleaching composition, its content is such that the total surfactant content in the ready-to-use composition ranges, for example, from 0.05% to 30% and, further, for example, from 0.1% to 20% by weight, relative to the total weight of the ready-to-use composition.

Cationic or Amphoteric Substantive Polymer

In one embodiment, the bleaching composition comprises at least one substantive polymer chosen from cationic and amphoteric substantive polymers. Polymers of this type make it possible to improve at least one of the cosmetic properties of the fibers (conditioning effect).

As used herein, the expression "cationic polymer" means any polymer comprising at least one group chosen from cationic groups and groups that may be ionized into cationic groups.

The cationic or amphoteric polymers that may, for example, be used in the compositions disclosed herein may be chosen from those already known per se as improving the cosmetic properties of the hair, i.e. those described in the Patent and Patent Application Nos. EP 337 354, FR 2 270 846, FR 2 383 660, FR 2 598 611, FR 2 470 596, FR 2 519 863, FR 2 788 974 and FR 2 788 976 for a list of these compounds.

The cationic polymers may, for example, be chosen from cationic polymers comprising at least one group chosen from primary, secondary, tertiary and quaternary amine groups, which may either form part of the main polymer chain or may be borne by a side substituent directly attached to the main polymer chain.

For example, the cationic polymers may be chosen from:
(1) copolymers of acrylamide and of dimethylaminoethyl methacrylate quaternized with dimethyl sulphate or with a dimethyl halide (HERCOFLOC from Hercules); copolymers of acrylamide and of methacryloyloxyethyltrimethylammonium chloride (BINA QUAT P 100 from Ciba Geigy); the copolymer of acrylamide and of methacryloyloxyethyltrimethylammonium methosulphate (RETEN from Hercules); quaternized or non-quaternized vinylpyrrolidone/dialkylaminoalkyl acrylate or methacrylate copolymers (GAFQUAT range from ISP; Copolymer 845, 958 and 937 from Gaf Corporation (ISP)); dimethylaminoethyl methacrylate/vinylcaprolactam/vinylpyrrolidone terpolymers (GAFFIX VC 713 from ISP); vinylpyrrolidone/methacrylamidopropyldimethylamine copolymers (STYLEZE CC 10 from ISP); vinylpyrrolidone/dimethylaminopropylmethacrylamide quaternized copolymers (Gafquat HS 100 from ISP);
(2) cellulose ether derivatives comprising quaternary ammonium groups, as described in French Patent No. 1 492 597. These polymers are also defined in the CTFA dictionary as quaternary ammoniums of hydroxyethylcellulose which has reacted with an epoxide substituted with a trimethylammonium group;
(3) cationic cellulose derivatives such as copolymers of cellulose or cellulose derivatives grafted with a water-soluble quaternary ammonium monomer, described, for example, in U.S. Pat. No. 4,131,576, such as hydroxyalkylcelluloses, for example, hydroxymethylcellulose, hydroxyethylcellulose and hydroxypropylcellulose grafted, for example, with a salt chosen from methacryloylethyltrimethylammonium, methacrylamidopropyltrimethylammonium and dimethyldiallylammonium salts;
(4) cationic polysaccharides described, for example, in U.S. Pat. Nos. 3,589,578 and 4,031,307, such as guar gums comprising trialkylammonium cationic groups. Guar gums modified with a salt, such as chloride, for example, guar gums modified with a salt of 2,3-epoxypropyltrimethylammonium chloride may be used;
(5) polymers comprising piperazinyl units and divalent alkylene or hydroxyalkylene radicals comprising straight or branched chains, optionally interrupted with at least one entity chosen from oxygen, sulphur and nitrogen atoms and aromatic and heterocyclic groups, and also the oxidation and/or quaternization products of these polymers. Such polymers are described, for example, in French Patent Nos. 2 162 025 and 2 280 361;
(6) water-soluble polyaminoamides prepared, for example, by polycondensation of an acidic compound with a polyamine, which are optionally crosslinked, optionally alkylated, or, if they comprise at least one tertiary amine functional group, quaternized. These polymers are described, for example, in French Patent Nos. 2 252 840 and 2 368 508;
(7) polyaminoamide derivatives resulting from the condensation of polyalkylene polyamines with polycarboxylic acids followed by an alkylation with difunctional agents. Examples of these polyaminoamide derivatives include adipic acid-dialkylaminohydroxyalkyldialkylenetriamine polymers wherein the alkyl radical is $C_1$-$C_4$. Such polymers are described, for example, in French Patent No. 1 583 363;
(8) polymers obtained by reacting a polyalkylene polyamine comprising two primary amine groups and at least one secondary amine group with a dicarboxylic acid chosen from diglycolic acid and saturated $C_3$-$C_8$ aliphatic dicarboxylic acids, and then with epichlorohydrin. Such polymers are described, for example, in U.S. Pat. Nos. 3,227,615 and 2,961,347;
(9) cyclopolymers of alkyldiallylamine and of dialkyldiallylammonium, in homopolymer or copolymer form, as described in French Patent No. 2 080 759 and in its Certificate of Addition No. 2 190 406;
(10) diquaternary ammonium polymers as described in Patent Nos. FR 2 320 330, FR 2 270 846, FR 2 316 271, FR 2 336 434, FR 2 413 907, U.S. Pat. No. 2,273,780, U.S. Pat. No. 2,375,853, U.S. Pat. No. 2,388,614, U.S. Pat. No. 2,454,547, U.S. Pat. No. 3,206,462, U.S. Pat. No. 2,261,002, U.S. Pat. No. 2,271,378, U.S. 3,874,870, U.S. Pat. No. 4,001,432, U.S. Pat. No. 3,929,990, U.S. Pat. No. 3,966,904, U.S. Pat. No. 4,005,193, U.S. Pat. No. 4,025,617, U.S. 4,025,627, U.S. Pat. No. 4,025,653, U.S. Pat. No. 4,026,945 and U.S. Pat. No. 4,027,020;

For example, cationic polymers comprising repeating units corresponding to the following formula below may be used in the compositions disclosed herein:

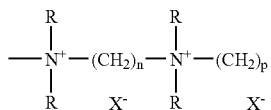

wherein: R, which may be identical or different, is chosen from C1-C4 alkyl radicals and hydroxyalkyl radicals; n and p, which may be identical or different, are each integers ranging from 2 to 20; and $X^-$ is an anion derived from a mineral or organic acid;

(11) poly(quaternary ammonium) polymers comprising repeating units of formula:

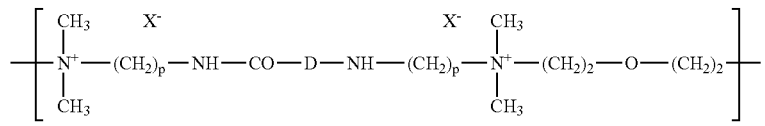

wherein: p is an integer ranging from 1 to 6; D may be nothing or may be chosen from —$(CH_2)_r$—CO— wherein r is a number equal to 4 or 7; and $X^-$ is chosen from anions. Such polymers may be prepared according to the processes described in U.S. Pat. No. 4,157,388, U.S. Pat. No. 4,702,906, U.S. Pat. No. 4,719,282 and EP 122 324;

(12) quaternary polymers of vinylpyrrolidone and of vinylimidazole;

(13) polyamines of the polyethylene glycol (15) tallow polyamine type (CTFA dictionary name); and

(14) crosslinked methacryloyloxy($C_1$-$C_4$)alkyltri($C_1$-$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound comprising olefinic unsaturation, for example, methylenebisacrylamide. A crosslinked acrylamide/methacryloyloxyethyltrimethylammonium chloride copolymer (20/80 by weight) in the form of a dispersion containing 50% by weight of the copolymer in mineral oil can be used, for example. This dispersion is sold under the name SALCARE SC 92 by the company Allied Colloids. A crosslinked methacryloyloxyethyltrimethylammonium chloride homopolymer containing about 50% by weight of the homopolymer in mineral oil or in a liquid ester can also be used. These dispersions are sold under the names SALCARE SC 95 and SALCARE SC 96 by the company Allied Colloids.

Further examples of cationic polymers that can be used in the compositions disclosed herein are polyalkyleneimines, for example, polyethyleneimines, polymers comprising at least one unit chosen from vinylpyridine and vinylpyridinium units, condensates of polyamines and of epichlorohydrin, quaternary polyureylenes and chitin derivatives.

The amphoteric polymers may, for example, be chosen from polymers comprising units K and M randomly distributed in the polymer chain, wherein K is a unit derived from a monomer comprising at least one basic nitrogen atom and M is a unit derived from an acidic monomer comprising at least one group chosen from carboxylic and sulphonic groups, or alternatively K and M, which may be identical or different, may be chosen from groups derived from zwitterionic carboxybetaine and sulphobetaine monomers;

K and M, which may be identical or different, may also be chosen from cationic polymer chains comprising at least one group chosen from primary, secondary, tertiary and quaternary amine groups, wherein at least one of the amine groups bears a carboxylic or sulphonic group linked via a hydrocarbon-based radical, or alternatively K and M, which may be identical or different, form part of a chain of a polymer comprising an α,β-dicarboxylic ethylene unit wherein one of the carboxylic groups has been made to react with a polyamine comprising at least one amine chosen from primary and secondary amines.

The amphoteric polymers corresponding to the above definition may be chosen, for example, from the following polymers:

(1) polymers resulting from the copolymerization of a monomer derived from a vinyl compound bearing a carboxylic group such as, acrylic acid, methacrylic acid, maleic acid, α-chloroacrylic acid, and a dialkyldiallylammonium salt such as dimethyldiallylammonium chloride, and a basic monomer derived from a substituted vinyl compound comprising at least one basic atom, such as, dialkylaminoalkyl methacrylate and acrylate, dialkylaminoalkylmethacrylamide and -acrylamide. Such compounds are described in U.S. Pat. No. 3,836,537. Mention may also be made of the sodium acrylate/acrylamidopropyltrimethylammonium chloride copolymer (POLYQUART KE 3033 by the company Henkel) and the acrylic acid/dimethyldiallylammonium chloride copolymer (MERQUAT 280, 295, Plus 3330, from Calgon);

(2) polymers comprising units derived from a) at least one monomer chosen from acrylamides and methacrylamides substituted on the nitrogen with an alkyl radical, for example, $C_2$-$C_{12}$ (such as ethyl, tert-butyl, tert-octyl, octyl, decyl and dodecyl), b) at least one acidic monomer comprising at least one reactive carboxylic group (for example acrylic acid, methacrylic acid, crotonic acid and itaconic acid, and monoesters of maleic and fumaric acids and anhydrides), and c) at least one basic monomer such as esters comprising at least one substituent chosen from primary, secondary, tertiary and quaternary amine substituents of acrylic acid, methacrylic acid, fumaric acid and maleic acid, and the product of quaternization of dimethylaminoethyl methacrylate with dimethyl and diethyl sulphate (for example aminoethyl, butylaminoethyl, N,N'-dimethylaminoethyl and N-tert-butylaminoethyl methacrylates).

Octylacrylamide/acrylate/butylaminoethyl methacrylate copolymers (AMPHOMER OR LOVOCRYL 47 by the company National Starch) may, for example, be used;

(3) crosslinked and partially or totally alkylated polyaminoamides, derived from polyaminoamides of general formula —[CO—R—CO-Z]— wherein R is chosen from divalent radicals derived from saturated and unsaturated dicarboxylic acids (for example adipic acid, 2,2,4-trimethyladipic acid, 2,4,4-trimethyladipic acid, terephthalic acid and itaconic acid), unsaturated monocarboxylic acids (for example, (meth)acrylic acid), $C_1$-$C_6$ alkyl esters of the abovementioned acids and radicals derived from the addition of one of these acids to a bis-primary or bis-secondary amine, and Z is chosen from radicals of a bis-primary, mono- and bis-secondary polyalkylenepolyamine. For example, Z represents
(a) from 60 to 100 mol %, of the radical —NH—[$(CH_2)_x$—NH]$_p$ wherein x=2 and p=2 or 3, or x=3 and p=2; this radical being derived from a compound chosen from diethylenetriamine, triethylenetetramine and dipropylenetriamine;
(b) from 0 to 40 mol %, of the above radical, wherein x=2 and p=1 and wherein the radical is derived from ethylenediamine, or the radical derived from piperazine —N[$CH_2CH_2$]$_2$N—;
(c) from 0 to 20 mol %, of the radical —NH—$(CH_2)_6$—NH— derived from hexamethylenediamine. The crosslinking agent for these polymers is a difunctional agent chosen from epihalohydrins, diepoxides, dianhydrides and bis-unsaturated derivatives, and alkylated by the action of acrylic acid, chloroacetic acid or an alkane sultone (for example, propane sultone or butane sultone) or the alkali metal salts thereof;
(4) polymers comprising at least one zwitterionic unit, for example, the butyl methacrylate/dimethylcarboxymethylammonioethyl methacrylate copolymer (DIAFORMER Z301 from Sandoz).
(5) Polymers derived from chitosan comprising monomer units corresponding to formulae (I), (II) and (III) below:

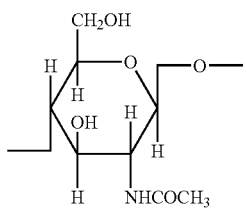

(I)

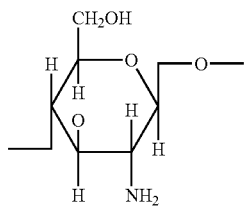

(II)

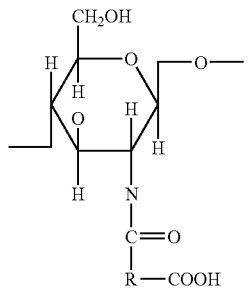

(III)

with unit (I) being present in proportions ranging from 0 to 30%, unit (II) in proportions ranging from 5% to 50% and unit (III) in proportions ranging from 30% to 90% wherein R is a radical of formula:

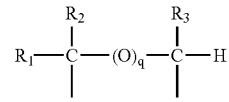

wherein q is equal to 0 or 1; and if q=0, $R_1$, $R_2$, and $R_3$, which may be identical or different, are each chosen from hydrogen, methyl, hydroxyl, acetoxy, amino, monoalkylamino and dialkylamino group, optionally interrupted with at least one nitrogen atom and/or optionally substituted with at least one substituent chosen from amine, hydoxyl and carboxyl, alkylthio optionally bearing an amino group, and sulphonic substituents; or, if q=1, $R_1$, $R_2$, and $R_3$, which may be identical or different, are each chosen from hydrogen and salts formed by these compounds with acids or bases;
(6) polymers derived from the N-carboxyalkylation of chitosan, such as N-carboxymethylchitosan and N-carboxybutylchitosan (EVALSAN from Jan Dekker);
(7) polymers as described in French Patent No. 1 400 366:

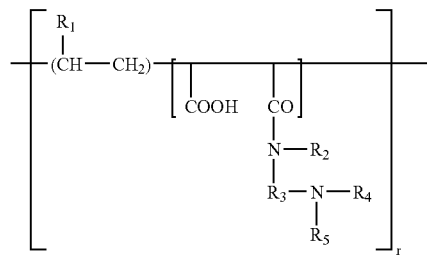

wherein $R_1$ is chosen from hydrogen, $CH_3O$—, $CH_3CH_2O$— and phenyl, $R_2$ and $R_5$, which may be identical or different, are each chosen from hydrogen and alkyls (such as methyl and ethyl), $R_4$ is chosen from alkyls (methyl and ethyl) and a radical of formula —$R_3$—N($R_5$)$_2$, wherein $R_3$ is chosen from —$(CH_2)_2$—, —$(CH_2)_3$— and —$CH_2$—CH($CH_3$)—, and also the higher homologues of these radicals and comprising up to 6 carbon atoms, and r is chosen such that the molecular weight of the polymer ranges from 500 to 6 000 000, such as from 1 000 to 1 000 000;
(8) amphoteric polymers of the type -D-X-D-X— chosen from:
a) polymers obtained by the action of chloroacetic acid or sodium chloroacetate on compounds comprising at least one unit of formula -D-X-D-X-D- wherein D is an —N[$CH_2CH_2$]$_2$N— (piperazinyl) radical and X is chosen from E and E', wherein E and E', which may be identical or different, are each chosen from divalent alkylene radicals comprising at least one chain chosen from straight and branched chains comprising up to 7 carbon atoms in the main chain, wherein the divalent alkylene radicals are optionally substituted with at least one hydroxyl group and can possibly also comprise at least one entity chosen from oxygen, nitrogen and sulphur and 1 to 3 aromatic and heterocyclic rings; the oxygen, nitrogen and sulphur atoms being present in the form of at least one group chosen from ether, thioether, sulphoxide, sulphone, sulphonium, alkylamine and alkenylamine groups, hydroxyl, benzylamine, amine oxide, quaternary ammonium, amide, imide, alcohol, ester and urethane groups;

b) polymers of formula -D-X-D-X— wherein D is an —N[CH$_2$CH$_2$]$_2$N— (piperazinyl) radical and X is chosen from E and E' and at least one X is chosen from E'; E having the meaning given above and E' being chosen from divalent alkylene radicals comprising at least one chain chosen from straight and branched chains comprising up to 7 carbon atoms in the main chain, wherein the divalent alkylene radicals are optionally substituted with at least one hydroxyl radicals and E' also comprising at least one nitrogen atom, the nitrogen atom being substituted with an alkyl chain, which is optionally interrupted by an oxygen atom, and wherein the alkyl chain comprises at least one functional group chosen from carboxyl and hydroxyl functional groups and betainized by reaction with chloroacetic acid or sodium chloroacetate; and (9) (C$_1$-C$_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also comprise other vinyl comonomers such as vinylcaprolactam.

For example, the cationic and amphoteric polymers that may be used in the compositions disclosed herein, may be chosen from:

(i) among the cationic polymers:
the dimethyldiallylammonium chloride homopolymer (MERQUAT 100 from Nalco);
copolymers of dimethyldiallylammonium chloride and of acrylamide (MERQUAT 2200 from Nalco);
polymers of poly(quaternary ammonium) prepared and described in French Patent No. 2 270 846, comprising repeating units of formulae (W) and (U) below:

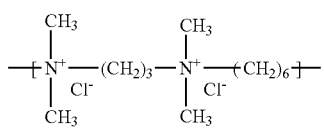

(W)

and, for example, those polymers with a molecular weight, determined by gel permeation chromatography, ranging from 9 500 to 9 900;

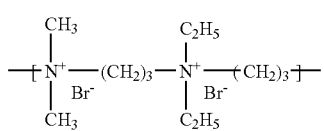

(U)

and, for example, those polymers with a molecular weight, determined by gel permeation chromatography, of about 1 200; and
polymers of poly(quaternary ammonium) of family (11) described above wherein X$^-$ is chlorine, and, for example, those polymers with a weight-average molecular mass of less than 100 000 and, for example, less than or equal to 50 000;

(ii) among the amphoteric polymers:
dimethyldiallylammonium chloride/acrylic acid copolyer (80/20) (MERQUAT 280 Dry from Calgon—CTFA name: POLYQUATERNIUM 22);
dimethyldiallylammonium chloride/acrylic acid copolymer (95/5) (MERQUAT 295 Dry from Calgon);
methacrylamidopropyltrimonium chloride, acrylic acid and ethyl acrylate copolymer (MERQUAT 2001 from Calgon —CTFA name: POLYQUATERNIUM 47); and
acrylamide/dimethyldiallylammonium chloride/acrylic acid terpolymer (MERQUAT Plus 3330 Dry from Calgon —CTFA name: POLYQUATERNIUM 39).

Other Additives

The at least one anhydrous bleaching composition may also comprise at least one mineral filler, for example, chosen from clays and silicas such as fumed silicas of hydrophilic or hydrophobic nature.

It may also comprise at least one binder such as vinylpyrrolidone, at least one lubricant, for example, chosen from polyolstearates and alkali metal and alkaline-earth metal stearates, and also agents for controlling the release of oxygen, such as magnesium carbonate or magnesium oxide.

The at least one anhydrous bleaching composition may comprise, where appropriate, at least one agent chosen from dyes, mattifying agents, for example, titanium oxides, sequestering agents, vitamins and provitamins, sunscreens, silicones and fragrances.

Needless to say, a person skilled in the art will take care to select the optional additional compound(s) mentioned above, such that the advantageous properties intrinsically associated with the at least one anhydrous bleaching composition and/or the ready-to-use bleaching composition are not, or are not substantially, adversely affected by the envisaged addition(s).

The at least one anhydrous bleaching composition, in paste form, may conventionally be prepared by dispersing, with mechanical stirring, all of the pulverulent compounds in the at least one inert liquid, in which the other liquid compounds of the bleaching composition have previously been dispersed or mixed.

The at least one anhydrous bleaching composition may also be prepared via extrusion, by introducing the liquid and solid phases of the composition into the extruder and then mixing them at a temperature below 25° C. using a co-rotating twin-screw system composed of transportation and blending members.

The oxidizing composition will now be described.

Oxidizing Composition

This composition is a hydrogen peroxide oil-in-water emulsion comprising at least one first surfactant chosen from nonionic and anionic surfactants and at least one copolymer comprising (a) at least one unit derived from a salified or non-salified (meth)acrylic acid and (b) at least one unit derived from esters of (meth)acrylic acid and at least one first fatty alcohol chosen from saturated and unsaturated, linear and branched, ethoxylated C$_8$-C$_{30}$ fatty alcohols.

Surfactants

The nonionic and anionic surfactants may be chosen from the surfactants in the lists detailed previously in the context of the description of the components constituting the at least one anhydrous bleaching composition.

For example, the at least one first surfactant may be chosen from polyalkoxylated and polyglycerolated, for example, polyethoxylated, nonionic surfactants. Examples of the at least one first surfactant include alcohols comprising a $C_8$-$C_{22}$ chain of carbon atoms, the number of ethylene oxide groups ranging from 1 to 50.

It should be noted that the content of the at least one first surfactant present in the at least one hydrogen peroxide oil-in-water emulsion may range, for example, from 0.05% to 30% by weight and, further, for example, from 0.1% to 20% by weight, relative to the total weight of the at least one hydrogen peroxide oil-in-water emulsion.

For example, the ready-to-use composition, i.e., the at least one anhydrous bleaching composition and the at least one hydrogen peroxide oil-in-water emulsion, may have a total surfactant content ranging, for example, from 0.05% to 30% by weight and, further, for example, from 0.1% to 20% by weight, relative to the total weight of the ready-to-use composition.

Copolymer

As indicated previously, the at least one copolymer present in the at least one hydrogen peroxide oil-in-water emulsion comprises (a) at least one unit derived from a salified or non-salified (meth)acrylic acid and (b) at least one unit derived from esters of (meth)acrylic acid and at least one first fatty alcohol chosen from saturated and unsaturated, linear and branched, ethoxylated $C_8$-$C_{30}$ fatty alcohols.

For example, the at least one unit derived from esters is obtained from an ester of acrylic or methacrylic acid and of a saturated $C_1$-$C_6$ and, for example, $C_1$-$C_4$ alcohol.

The at least one unit derived from acids present in the at least one copolymer may optionally be totally or partially neutralized with at least one agent chosen from mineral and organic alkaline agents.

Optionally, the at least one copolymer may comprise units derived from at least one polyethylenically unsaturated monomer, chosen, for example, from diallyl phthalate, divinylbenzene, allyl methacrylate and ethylene glycol dimethacrylate.

The methacrylic acid/ethyl acrylate/stearyl methacrylate oxyethylenated copolymer (55/35/10) and the (meth)acrylic acid/ethyl acrylate/behenyl methacrylate 25 EO oxyethylenated copolymer are suitable for use in the compositions disclosed herein.

For example, the at least one copolymer may comprise at least one unit derived from (meth)acrylic acid, at least one unit derived from an alkyl acrylate (such as ethyl acrylate) and at least one unit derived from ethoxylated behenyl methacrylate, for example, comprising 25 mol of ethylene oxide.

This type of polymer is well known and is sold, for example, by Rohm & Haas under the name ACULYN 28.

In one embodiment, the at least one copolymer is present, for example, in an amount ranging from 0.005% to 15% by weight, further, for example, from 0.05% to 7.5% by weight, and, even further, for example, from 0.1% to 5% by weight, relative to the total weight of the ready-to-use composition.

Oil Phase of the Emulsion

The oil phase of the emulsion may, for example, comprise at least one second fatty alcohol.

As used to define the at least one second fatty alcohol, the term "fatty alcohol" means any saturated or unsaturated, linear or branched fatty alcohol. Among these fatty alcohols, $C_{12}$-$C_{22}$ alcohols may, for example, be used.

For example, the at least one second fatty alcohol may be chosen from lauryl alcohol, cetyl alcohol, stearyl alcohol, oleyl alcohol, behenyl alcohol, linoleyl alcohol, undecylenyl alcohol, palmitoleyl alcohol, linolenyl alcohol, arachidonyl alcohol and erucyl alcohol. Cetyl alcohol may, for example, be used.

In the at least one hydrogen peroxide oil-in-water emulsion, the at least one second fatty alcohol may be present in an amount ranging from 0.1% to 30% by weight and further, for example, from 0.5% to 15% by weight, relative to the total weight of the at least one hydrogen peroxide oil-in-water emulsion.

Additives

The at least one hydrogen peroxide oil-in-water emulsion may also comprise at least one additive that is common in the field, for example, at least one additive chosen from sequestering agents such as ethylenediaminetetraacetic acid, pentasodium pentetate (CTFA name) and etidronic acid; hydrogen peroxide stabilizers such as alkali metal (such as sodium and potassium) stannate and pyrophosphate salts, and sodium salicylate; colorants; fragrances; antifoams; and cationic and amphoteric substantive polymers such as those described above.

Needless to say, a person skilled in the art will take care to select the optional additional compound(s) mentioned above, such that the properties of the ready-to-use bleaching composition are not, or are not substantially, adversely affected by the envisaged addition(s).

The content of hydrogen peroxide in the at least one hydrogen peroxide oil-in-water emulsion may, for example, range from 1% to 12% by weight as hydrogen peroxide titre, further, for example, from 2% to 12% by weight, as hydrogen peroxide titre, and, even further, for example, from 2.7% to 12% by weight, as hydrogen peroxide titre.

The hydrogen peroxide, in the at least one ready-to-use bleaching composition, may be present, for example, in an amount ranging from 1% to 12% by weight, as hydrogen peroxide titre, further, for example, from 2% to 9% by weight, as hydrogen peroxide titre and, even further, for example, from 2% to 6% by weight, as hydrogen peroxide titre.

For example, the pH of the at least one hydrogen peroxide oil-in-water emulsion may range from 1 to 6 and, further, for example, from 2 to 4.

The acidic pH ensures the stability of the hydrogen peroxide in the at least one hydrogen peroxide oil-in-water emulsion. The acidic pH may be obtained by using at least one acidifying agent, for example, chosen from hydrochloric acid, acetic acid, phosphoric acid, lactic acid, citric acid, salicylic acid and boric acid.

In addition, the pH may be conventionally adjusted, if necessary, by adding at least one basifying agent, for example, chosen from aqueous ammonia, monoethanolamine, diethanolamine, triethanolamine, isopropanolamine, 1,3-diaminopropane, alkaline and ammonium (bi)carbonate, organic carbonate such as guanidine carbonate, and alkaline hydroxide, it being possible, obviously, for all these compounds to be taken alone or as a mixture.

The at least one hydrogen peroxide oil-in-water emulsion is prepared by mixing at room temperature the hydrogen peroxide and the other ingredients of the aqueous phase of the oil-in-water emulsion and then preparing the emulsion by adding the oil phase of the emulsion, at a temperature above room temperature.

The process for preparing the ready-to-use bleaching composition disclosed herein comprises mixing the at least one anhydrous bleaching composition and the at least one hydrogen peroxide oil-in-water emulsion. This mixing must be performed immediately before applying the product to the fibers to be bleached.

Usually, the at least one anhydrous bleaching composition is mixed with 0.5 to 10 equivalents by weight, of the at least one hydrogen peroxide oil-in-water emulsion.

It should be noted that the pH of the ready-to-use composition disclosed herein may range, for example, from 4 to 12, further, for example, from 7 to 11.5 and, even further, for example, from 8 to 11.

Further disclosed herein is a process for bleaching human keratin fibers, such as hair, comprising applying at least one ready-to-use bleaching composition to the area of the wet or dry human keratin fibers to be bleached; leaving the at least one ready-to-use bleaching composition on the human keratin fibers to act for a leave-in time that is sufficient to obtain the desired bleaching result; removing the at least one ready-to-use bleaching composition from the human keratin fibers by rinsing with water, washing the human keratin fibers with shampoo and optionally drying the human keratin fibers.

The leave-in time may range, for example, from 1 to 60 minutes and, further, for example, from 10 to 50 minutes.

Further disclosed herein is a multi-compartment device or "kit" for performing the process for bleaching human keratin fibers.

This device comprises at least two compartments, wherein
at least one compartment comprises at least one anhydrous bleaching composition, in paste form, comprising:
  at least one peroxygenated salt,
  at least one alkaline agent, and
  from 15% to 35% by weight of at least one inert organic liquid; and
at least one other compartment comprising at least one hydrogen peroxide oil-in-water emulsion comprising:
  at least one first surfactant chosen from nonionic and anionic surfactants and
  at least one copolymer comprising (a) at least one unit derived from a salified or non-salified (meth)acrylic acid and (b) at least one unit derived from esters of (meth)acrylic acid and at least one first fatty alcohol chosen from saturated and unsaturated, linear and branched, ethoxylated $C_8$-$C_{30}$ fatty alcohols.

Non-limiting examples of various embodiments disclosed herein will now be given.

EXAMPLES

Bleaching Composition A in Anhydrous Paste Form
Composition A below was prepared:

| | Amount (g %) |
|---|---|
| Potassium persulphate | 41.3 |
| Sodium disilicate | 18 |
| Ammonium chloride | 2.2 |
| Ammonium sulphate | 2 |
| EDTA | 0.2 |
| Hexamethyl diisocyanate/polyethylene glycol copolymer containing α and ω stearyl polyoxyethylene end groups (SER-AD FX 1100 - Servo Delden) | 0.5 |
| Weakly crosslinked carboxymethyl potato starch/sodium salt (Primojel from Avebe) | 1 |
| Guar gum | 0.5 |
| Xanthan gum | 2 |
| Titanium oxide | 1 |
| Sodium cetostearyl sulphate | 2 |
| Sodium lauryl sulphate | 2 |
| Magnesium stearate | 2 |
| Ultramarine | 0.5 |
| Isopropyl myristate (Cognis) | 24.2 |
| Fumed silica of hydrophilic nature (Aerosil 300 - Degussa Hüls) | 0.6 |

Oxidizing Compositions (O/W Emulsions)
The emulsions below were prepared:

| | B (g %) | C (g %) | D (g %) | E (g %) |
|---|---|---|---|---|
| Cetyl alcohol | 8 | 8 | 10 | 8 |
| Cetyl alcohol (20 EO) | 2 | 2 | 2 | 4 |
| Glycerol | 0.5 | 0.5 | 0.5 | 0.5 |
| Acrylate/beheneth-25 methacrylate copolymer (Aculyn 28 - ISP/Rohm & Haas) | 2 | / | / | / |
| Tetrasodium pyrophosphate | 0.04 | 0.04 | 0.04 | 0.04 |
| Sodium etidronate | 0.2 | 0.2 | 0.2 | 0.2 |
| Aqueous 50% hydrogen peroxide solution | 18 | 18 | 18 | 18 |
| 85% phosphoric acid | qs pH 3 | qs pH 3 | qs pH 3 | qs pH 3 |
| Water | qs 100 g | qs 100 g | qs 100 g | qs 100 g |

Ready-to-use Aqueous Bleaching Compositions
Comp. A/B: 20 g of bleaching composition A+30 g of oxidizing composition B
Comp. A/C: 20 g of bleaching composition A+30 g of oxidizing composition C
Comp. A/D: 20 g of bleaching composition A+30 g of oxidizing composition D
Comp. A/E: 20 g of bleaching composition A+30 g of oxidizing composition E
The compositions were obtained by mixing.

Evaluation of the Speed of Mixing of the Ready-to-use Agueoous Bleaching Compositions
Evaluated the mixing time in seconds (cf. via a chronometer)
Started the chronometer when the spatula entered the mixture
Stopped the chronometer when the mixtures was smooth and uniform
Evaluated by a panel of 5 individuals

| | Comp. A/B | Comp. A/C | Comp. A/D | Comp. A/E |
|---|---|---|---|---|
| Evaluation of the mixing time/mean (seconds) | 65 | 94 | 84 | 91 |
| Standard deviation (seconds) | 6 | 6 | 6 | 5 |

The mixture of compositions A and B (Comp. A/B), prepared according to the present disclosure, was significantly faster to prepare.

Furthermore, the ready-to-use bleaching composition Comp. A/B applied easily and quickly. It showed very good adhesion. It did not run outside the areas of hair that was desired to bleach. Finally, it provided strong and uniform bleaching, while at the same time afforded at least one very good cosmetic property.

What is claimed is:

1. A ready-to-use composition for bleaching human keratin fibers, comprising:
   i) at least one anhydrous bleaching composition, in paste form, comprising:
      at least one peroxygenated salt;
      at least one alkaline agent; and
      from 15% to 35% by weight of at least one inert organic liquid; and
   ii) at least one hydrogen peroxide oil-in-water emulsion comprising:
      at least one first surfactant chosen from nonionic and anionic surfactants and
      at least one copolymer comprising (a) at least one unit derived from a salified or non-salified (meth)acrylic acid and (b) at least one unit derived from esters of (meth)acrylic acid and at least one first fatty alcohol chosen from saturated and unsaturated, linear and branched, ethoxylated $C_8$-$C_{30}$ fatty alcohols,
   wherein said at least one anhydrous bleaching composition and said at least one hydrogen peroxide oil-in-water emulsion are mixed together before use.

2. The ready-to-use composition according to claim 1, wherein the human keratin fibers are hair.

3. The ready-to-use composition according to claim 1, wherein the at least one inert organic liquid is chosen from polydecenes, carboxylic acid monoesters and polyesters, sugar monoesters and polyesters of $C_8$-$C_{30}$ acids, cyclic ethers, cyclic esters, silicone oils, mineral oils, and plant oils.

4. The ready-to-use composition according to claim 1, wherein the at least one inert organic liquid is chosen from saturated and unsaturated, linear and branched carboxylic acid monoesters and polyesters comprising at least one hydrogen-based chain comprising $C_8$-$C_{30}$ carbons.

5. The ready-to-use composition according to claim 1, wherein the at least one peroxygenated salt is chosen from alkali metal and alkaline-earth metal persulphates, alkali metal and alkaline-earth metal perborates, alkali metal and alkaline-earth metal percarbonates and alkali metal and alkaline-earth metal peroxides.

6. The ready-to-use composition according to claim 1, wherein the at least one peroxygenated salt is chosen from sodium persulphate and potassium persulphate.

7. The ready-to-use composition according to claim 1, wherein the at least one peroxygenated salt is present in the at least one anhydrous bleaching composition in an amount ranging from 10% to 70% by weight, relative to the total weight of the at least one anyhydrous bleaching composition.

8. The ready-to-use composition according to claim 7, wherein the at least one peroxygenated salt is present in the at least one anhydrous bleaching composition in an amount ranging from 20% to 60% by weight, relative to the total weight of the at least one anyhydrous bleaching composition.

9. The ready-to-use composition according to claim 1, wherein the at least one peroxygenated salt is present in the ready-to-use composition in an amount ranging from 5% to 35% by weight, relative to the total weight of the ready-to-use composition.

10. The ready-to-use composition according to claim 9, wherein the at least one peroxygenated salt is present in the ready-to-use composition in an amount ranging from 10% to 30% by weight, relative to the total weight of the ready-to-use composition.

11. The ready-to-use composition according to claim 1, wherein the at least one alkaline agent is chosen from urea; ammonium salts; alkali metal silicates, phosphates and carbonates; and alkaline-earth metal silicates, phosphates and carbonates.

12. The ready-to-use composition according to claim 1, wherein the at least one alkaline agent is present in the at least one anhydrous bleaching composition in an amount ranging from 0.01% to 40% by weight, relative to the total weight of the at least one anhydrous bleaching composition.

13. The ready-to-use composition according to claim 12, wherein the at least one alkaline agent is present in the at least one anhydrous bleaching composition in an amount ranging from 0.1% to 30% by weight, relative to the total weight of the at least one anhydrous bleaching composition.

14. The ready-to-use composition according to claim 1, wherein the at least one alkaline agent is present in the ready-to-use composition in an amount ranging from 0.005% to 20% by weight, relative to the total weight of the ready-to-use composition.

15. The ready-to-use composition according to claim 14, wherein the at least one alkaline agent is present in the ready-to-use composition in an amount ranging from 0.05% to 15% by weight, relative to the total weight of the ready-to-use composition.

16. The ready-to-use composition according to claim 1, wherein the at least one anhydrous bleaching composition further comprises at least one water-soluble thickener not comprising a hydrophobic chain.

17. The ready-to-use composition according to claim 16, wherein the at least one water-soluble thickener is present in the at least one anhydrous bleaching composition in an amount ranging from 0.01% to 30% by weight, relative to the total weight of the at least one anhydrous composition.

18. The ready-to-use composition according to claim 1, wherein the at least one anhydrous bleaching composition further comprises at least one second surfactant chosen from non ionic, anionic, amphoteric, zwitterionic and cationic surfactants.

19. The ready-to-use composition according to claim 1, wherein the at least one anhydrous bleaching composition further comprises at least one amphiphilic polymer comprising at least one hydrophobic chain.

20. The ready-to-use composition according to claim 19, wherein the at least one amphiphilic polymer comprising at least one hydrophobic chain is different from the at least one copolymer present in the at least one hydrogen peroxide oil-in-water emulsion.

21. The ready-to-use composition according to claim 19, wherein the at least one amphiphilic polymer comprising at least one hydrophobic chain is present in the ready-to-use composition in an amount ranging from 0.01% to 30% by weight, relative to the total weight of the ready-to-use composition.

22. The ready-to-use composition according to claim 1, wherein the at least one anhydrous bleaching composition further comprises at least one substantive polymer chosen from cationic and associative substantive polymers.

23. The ready-to-use composition according to claim 1, wherein the at least one anhydrous bleaching composition comprises less than 1% by weight of water, relative to the total weight of the at least one anhydrous bleaching composition.

24. The ready-to-use composition according to claim 23, wherein the at least one anhydrous bleaching composition comprises less than 0.5% by weight of water, relative to the total weight of the anhydrous bleaching composition.

25. The ready-to-use composition according to claim 1, wherein the at least one copolymer present in the at least one hydrogen peroxide oil-in-water emulsion comprises at least one unit derived from esters of (meth)acrylic acid and saturated $C_1$-$C_6$ ethoxylated alcohols.

26. The ready-to-use composition according to claim 25, wherein the saturated $C_1$-$C_6$ ethoxylated alcohols are chosen from $C_1$-$C_2$ ethoxylated alcohols.

27. The ready-to-use composition according to claim 1, wherein the at least one copolymer comprises at least one unit derived from (meth)acrylic acid, at least one unit derived from ethyl acrylate and at least one unit derived from ethoxylated behenyl (meth)acrylate.

28. The ready-to-use composition according to claim 27, wherein the at least one unit derived from ethoxylated behenyl (meth)acrylate comprises 25 mol of ethylene oxide.

29. The ready-to-use composition according to claim 1, wherein the at least one copolymer is present in the ready-to-use composition in an amount ranging from 0.005% to 15% by weight, relative to the total weight of the ready-to-use composition.

30. The ready-to-use composition according to claim 29, wherein the at least one copolymer is present in the ready-to-use composition in an amount ranging from 0.05% to 7.5% by weight, relative to the total weight of the ready-to-use composition.

31. The ready-to-use composition according to claim 30, wherein the at least one copolymer is present in the ready-to-use composition in an amount ranging from 0.1% to 5% by weight, relative to the total weight of the ready-to-use composition.

32. The ready-to-use composition according to claim 1, wherein the at least one first surfactant is chosen from polyalkoxylated and polyglycerolated nonionic surfactants.

33. The ready-to-use composition according to claim 32, wherein the at least one first surfactant is chosen from polyethoxylated non-ionic surfactants.

34. The ready-to-use composition according to claim 1, wherein the at least one first surfactant is present in the ready-to-use composition in an amount ranging from 0.05% to 30% by weight, relative to the total weight of the ready-to-use composition.

35. The ready-to-use composition according to claim 34, wherein the at least one first surfactant is present in the ready-to-use composition in an amount ranging from 0.1% to 20% by weight, relative to the total weight of the ready-to-use composition.

36. The ready-to-use composition according to claim 1, wherein the oil phase of the at least one hydrogen peroxide oil-in-water emulsion comprises at least one second fatty alcohol.

37. The ready-to-use composition according to claim 1, wherein the hydrogen peroxide in the ready-to-use composition is present in an amount ranging from 1% to 12% by weight, as hydrogen peroxide titre.

38. The ready-to-use composition according to claim 37, wherein the hydrogen peroxide in the ready to use composition is present in an amount ranging from 2% to 9% by weight, as hydrogen peroxide titre.

39. The ready-to-use composition according to claim 38, wherein the hydrogen peroxide in the ready to use composition is present in an amount ranging from 2% to 6%, by weight as hydrogen peroxide titre.

40. The ready-to-use composition according to claim 1, wherein the pH of the at least one hydrogen peroxide oil-in-water emulsion ranges from 1 to 6.

41. The ready-to-use composition according to claim 40, wherein the pH of the at least one hydrogen peroxide oil-in-water emulsion ranges from 2 to 4.

42. The ready-to-use composition according to claim 1, wherein the pH of the ready-to-use composition ranges from 4 to 12.

43. The ready-to-use composition according to claim 42, wherein the pH of the ready-to-use composition ranges from 7 to 11.5.

44. The ready-to-use composition according to claim 43, wherein the pH of the ready-to-use composition ranges from 8 to 11.

45. A process for preparing a ready-to-use composition for bleaching human keratin fibers, comprising mixing before use:
   i) at least one anhydrous bleaching composition, in paste form, comprising:
      at least one peroxygenated salt;
      at least one alkaline agent; and
      from 15% to 35% by weight of at least one inert organic liquid; and
   ii) at least one hydrogen peroxide oil-in-water emulsion comprising:
      at least one first surfactant chosen from nonionic and anionic surfactants and
      at least one copolymer comprising (a) at least one unit derived from a salified or non-salified (meth)acrylic acid and (b) at least one unit derived from esters of (meth)acrylic acid and at least one first fatty alcohol chosen from saturated and unsaturated, linear and branched, ethoxylated $C_8$-$C_{30}$ fatty alcohols.

46. The process according to claim 45, wherein the human keratin fibers are hair.

47. A process for bleaching human keratin fibers comprising,
   (1) applying, to the area of wet or dry human keratin fibers to be bleached, at least one ready-to-use bleaching composition comprising,
      i) at least one anhydrous bleaching composition, in paste form, comprising:
         at least one peroxygenated salt;
         at least one alkaline agent; and
         from 15% to 35% by weight of at least one inert organic liquid; and
      ii) at least one hydrogen peroxide oil-in-water emulsion comprising:
         at least one first surfactant chosen from nonionic and anionic surfactants and
         at least one copolymer comprising (a) at least one unit derived from a salified or non-salified (meth)acrylic acid and (b) at least one unit derived from esters of (meth)acrylic acid and at least one first fatty alcohol chosen from saturated and unsaturated, linear and branched, ethoxylated $C_8$-$C_{30}$ fatty alcohols;
   (2) leaving the at least one ready-to-use composition on the human keratin fibers to act for a leave-in time sufficient to obtain a desired bleaching result;
   (3) removing the at least one ready-to-use composition from the human keratin fibers by rinsing with water; and
   (4) washing the human keratin fibers with shampoo and optionally drying the human keratin fibers.

48. The process according to claim 47, wherein the human keratin fibers are hair.

49. The bleaching process according to claim 47, wherein the leave-in time ranges from 1 to 60 minutes.

50. The bleaching process according to claim 49, wherein the leave-in time ranges from 10 to 50 minutes.

51. A multi-compartment device comprising at least two compartments wherein,
- at least one compartment comprises at least one anhydrous bleaching composition, in paste form, comprising:
  - at least one peroxygenated salt,
  - at least one alkaline agent, and
  - from 15% to 35% by weight of at least one inert organic liquid; and
- at least one other compartment comprising at least one hydrogen peroxide oil-in-water emulsion comprising
  - at least one first surfactant chosen from nonionic and anionic surfactants and
  - at least one copolymer comprising (a) at least one unit derived from a salified or non-salified (meth)acrylic acid and (b) at least one unit derived from esters of (meth)acrylic acid and at least one first fatty alcohol chosen from saturated and unsaturated, linear and branched, ethoxylated $C_8$-$C_{30}$ fatty alcohols.

* * * * *